US009757440B2

(12) United States Patent
Bzik et al.

(10) Patent No.: US 9,757,440 B2
(45) Date of Patent: *Sep. 12, 2017

(54) METHOD FOR TREATING CANCER WITH *TOXOPLASMA GONDII* VACCINE (75) Inventors: David J. Bzik, Grantham, NH (US); Barbara A. Fox, Grantham, NH (US); Steven N. Fiering, Orange, NH (US); Jose R. Conejo-Garcia, Philadelphia, PA (US); Jason Baird, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 502 days.

This patent is subject to a terminal disclaimer.

(21) Appl. No.: 13/276,577

(22) Filed: Oct. 19, 2011

(65) Prior Publication Data
US 2012/0045477 A1 Feb. 23, 2012

Related U.S. Application Data (63) Continuation-in-part of application No. 12/754,970, filed on Apr. 6, 2010, now Pat. No. 8,282,942, which is a continuation-in-part of application No. 12/394,365, filed on Feb. 27, 2009, now Pat. No. 7,803,389, which is a continuation-in-part of application No. PCT/US2008/081274, filed on Oct. 27, 2008.

(60) Provisional application No. 60/983,339, filed on Oct. 29, 2007, provisional application No. 61/057,972, filed on Jun. 2, 2008.

(51) Int. Cl.
| | | |
|---|---|---|
| *A61K 39/00* | (2006.01) |
| *A61K 39/002* | (2006.01) |
| *C12N 1/00* | (2006.01) |
| *G01N 33/569* | (2006.01) |
| *A61K 39/015* | (2006.01) |
| *C12N 1/36* | (2006.01) |
| *C12N 9/90* | (2006.01) |
| *C12N 9/00* | (2006.01) |

(52) U.S. Cl.
CPC .......... *A61K 39/015* (2013.01); *A61K 39/002* (2013.01); *C12N 1/36* (2013.01); *C12N 9/90* (2013.01); *C12N 9/93* (2013.01); *A61K 2039/522* (2013.01); *A61K 2039/523* (2013.01); *A61K 2039/585* (2013.01)

(58) Field of Classification Search
None
See application file for complete search history.

(56) References Cited

U.S. PATENT DOCUMENTS

| | | | | |
|---|---|---|---|---|
| 6,214,888 B1 * | 4/2001 | Ren et al. | .................... | 514/729 |
| 7,803,389 B2 * | 9/2010 | Bzik et al. | ................. | 424/273.1 |
| 8,673,289 B2 * | 3/2014 | Bzik et al. | .................. | 424/93.1 |
| 2005/0287648 A1 | 12/2005 | Smith et al. | ................. | 435/91.1 |
| 2009/0181056 A1 | 7/2009 | Bzik et al. | ................. | 424/273.1 |
| 2010/0203085 A1 | 8/2010 | Bzik et al. | ................. | 424/273.1 |
| 2010/0221246 A1 | 9/2010 | Goydos et al. | ............ | 424/133.1 |

FOREIGN PATENT DOCUMENTS

WO   WO 2005/009463 A2 *   2/2005   ............. A61K 39/04

OTHER PUBLICATIONS

Ju-Ock Kim et al. Inhibition of Lewis Lung Carcinoma Growth by Toxoplasma gondii through Induction of Th1 Immune Responses and Inhibition of Angiogenesis. J Korean Med Sci Sep. 2007; 22 (Suppl): S38-46.*
J C Schwab, Y Cao, M R Slowik, and K A Joiner. Localization of azithromycin in Toxoplasma gondii-infected cells. Antimicrob Agents Chemother. Jul. 1994; 38(7): 1620-1627.*
Charest et al. Recombinant Attenuated Toxoplasma gondii Expressing the Plasmodium yoelii Circumsporozoite Protein Provides Highly Effective Priming for CD8_T Cell-Dependent Protective Immunity Against Malaria J Immunol 2000; 165:2084-2092.*
Chhabra MB, Mahajan RC, Ganguly NK. Effects of 60Co irradiation on virulent Toxoplasma gondii and its use in experimental immunization.Int J Radiat Biol Relat Stud Phys Chem Med. May 1979;35(5):433-40.*
Barbara A. Fox & David J. Bzik. De novo pyrimidine biosynthesis is required for virulence of Toxoplasma gondii. Nature 415, 926-929 (Feb. 21, 2002).*
Aosai F, Yang TH, Ueda M, Yano A. Isolation of naturally processed peptides from a Toxoplasma gondii-infected human B lymphoma cell line that are recognized by cytotoxic T lymphocytes.J Parasitol. Apr. 1994;80(2):260-6.*
Robert G. K. Donald et al. Toxoplasma gondii Cyclic GMP-Dependent Kinase: Chemotherapeutic Targeting of an Essential Parasite Protein Kinase. Eukaryotic Cell, Jun. 2002, p. 317-328.*
Yasuhiro Suzuki et al.Antitumor Effect of Formalin-Fixed Toxoplasma gondii Organisms on EL4 Lymphoma in Toxoplasma-Infected Mice. Journal of Biological Response Modifiers 5:288-293 (1986).*
Drew M. Pardoll. Vaccines: Spinning molecular immunology into successful immunotherapy. Nature Reviews Immunology 2, 227-238 (Apr. 2002).*
Ju-Ock Kim et al. Inhibition of Lewis Lung Carcinoma Growth by Toxoplasma gondii through Induction of Th1 Immune Responses and Inhibition of Angiogenesis. J Korean Med Sci Sep. 2007; 22 (Supply) S38-46.*
Carlos S. Subauste et al., Human Dendritic Cells Discriminate Between Viable and Killed Toxoplasma gondii Tachyzoites: Dendritic Cell Activation After Infection with Viable Parasites Results in CD28 and CD40 Ligand Signaling That Controls IL-12-Dependent and-Independent T Cell Production of IFN-g1. J Immunol 2000; 165:1498-1505.*
Fong et al., Dendritic Cells in Cancer Immunotherapy. Annu. Rev. Immunol. 2000. 18:245-273.*
Schuler et al., The use of dendritic cells in cancer immunotherapy. Current Opinion in Immunology 2003, 15:138-147.*

(Continued)

*Primary Examiner* — Kevin Hill
*Assistant Examiner* — Arthur S Leonard
(74) *Attorney, Agent, or Firm* — Licata & Tyrrell P.C.

(57) ABSTRACT

The present invention provides attenuated *Toxoplasma gondii* mutants for use as vaccines in the prevention or treatment of cancer.

2 Claims, 3 Drawing Sheets (56) References Cited

OTHER PUBLICATIONS

Hobohm, U. Fever and cancer in perspective. Cancer Immunol Immunother. 2001, 50:391-396.*

Narkia, M. Coley's Toxins/Issel's Fever Therapy, Cancer Guide: Alternative and Complementary Therapies. Apr. 1996. p. 1-6 http://cancerguide.org/coley.html.*

Aravind, L. and Koonin, E. V. "Prokaryote Homologs of the Eukaryotic DNA-End-Binding Protein Ku, Novel Domains in the Ku Protein and Prediction of a Prokaryotic Double-Strand Break Repair System" Genome Research 2001 11:1365-1374.

Bauman, P. and Cech, T. R. "Protection of the Telomeres by the Ku Protein in the Fission Yeast" Molecular Biology of the Cell 2000 11:3265-3275.

Burton et al. "Ku Heterodimer-Independent End Joining in *Trypanosoma brucei* Cell Extracts Relies upon Sequence Microhomology" Eukaryotic Cell 2007 6(10):1773-1781.

Darani et al. "Effects of *Toxoplasma gondii* and *Toxocara canis* Antigens on WEHI-164 Fibrosarcoma Growth in a Mouse Model" The Korean Journal of Parasitology 2009 47(2):175-177.

Doherty et al. "Indentification of Bacterial Homologues of the Ku DNA Repair Proteins" Federation of European Biochemical Societies Letters 2001 500:186-188.

Featherstone, C. and Jackson, S. P. "Ku, a DNA Repair Protein with Multiple Cellular Functions?" Mutation Research 1999 434:3-15.

Fox, B. A. and Bzik, D. J. "De Novo Pyrimidine Biosynthesis Is Required for Virulence of*Toxoplasma gondii*" Nature 2002 415:926-929.

Gottstein, B. "Toxoplasma gondii: Perspectives for a Vaccine" Schweiz Med Wochenschr Suppl. 1995 65:89S-95S.

Hopfner et al. "DNA Double-Stranded Break Repair from Head to Tail"Current Opinion in Structural Biology 2002 12:115-122.

Hoppner, W. "Clinical Impact of Molecular Diagnostics in Endocrinology. Polymorphisms, Mutations and DNA Technologies" Hormone Research 2002 58 Suppl. (3) :7-15 Abstract.

Hunter et al. "Cutting Edge: Systemic Inhibition of Angiogenesis Underlies Resistance to Tumors During Acute Toxoplasmosis" The Journal of Immunology 2001 166:5878-5881.

Kim et al. "Inhibition of Lewis Lung Carcinoma Growth by *Toxoplasma gondii* through Induction of Th1 Immune Responses and Inhibition of Angiogenesis" Journal of Korean Medical Science 2007 22(Suppl):S38-46.

Kleppe et al. "Why Do Mutations Cause Disease—a Protein Chemical Perspective" Tidsskr Nor Laegeforen 2001 121(23):2717-20 Abstract.

Motamedi et al. "Improvement of a Dendritic Cell-based Therapeutic Cancer Vaccine with Components of *Toxoplasma gondii*" Clinical and Vaccine Immunology 2009 16(10) :1393-1398.

Ninomiya et al. "Highly Efficienct Gene Replacements in *Neurospora* Strains Deficient for Nonhomologous End-Joining" Proceedings of the National Academy of Sciences 2004 101(33) :12248-12253.

Sandoval, A. and Labhart, P. "High G/C Content of Cohesive Overhangs Renders DNA End Joining Ku-Independent" DNA Repair 2004 3:13-21.

Suzuki et al. "Antitumor Effect of Formalin-fixed *Toxoplasma gondii* Organisms of EL4 Lymphoma in *Toxoplasma*-infected Mice" Journal of Biological Response Modifiers 1986 5(4) :288-293.

The Institute for Genomic Research Accession No. 583.m05492.

Waldeland, H. and Frenkel, J. K. "Live and Killed Vaccines Against Toxoplasmosis in Mice" Journal of Parasitology 1983 69(1) :60-5 Abstract.

Walker et al. "Structure of the Ku Heterodimer Bound to DNA and its Implications for Double-Strand Break Repair" Nature 2001 412:607-614.

Yoo, S. and Dynan, W. S. "Characterization of the RNA Binding Properties of Ku Protein" Biochemistry 1998 37:1336-1343.

Office Communication dated Oct. 19, 2009 from U.S. Appl. No. 12/394,365, filed Feb. 27, 2009.

Office Communication dated Jan. 25, 2010 from U.S. Appl. No. 12/394,365, filed Feb. 27, 2009.

International Search Report from PCT/US2012/060746, dated Mar. 13, 2013.

* cited by examiner

METHOD FOR TREATING CANCER WITH *TOXOPLASMA GONDII* VACCINE

This application is a continuation-in-part application of U.S. patent application Ser. No. 12/754,970, filed Apr. 6, 2010, which is a continuation-in-part application of U.S. patent application Ser. No. 12/394,365, filed Feb. 27, 2009, now U.S. Pat. No. 7,803,389, which is a continuation-in-part application of PCT/US2008/081274, filed Oct. 27, 2008, which claims benefit of priority to U.S. Provisional Application Ser. Nos. 60/983,339, filed Oct. 29, 2007, and 61/057,972, filed Jun. 2, 2008, the contents of which are incorporated herein by reference in their entireties.

This invention was made with government support under contract numbers RO1 AI041930, RO1 CA124515 and RO1 CA120777 awarded by the National Institutes of Health. The government has certain rights in the invention.

BACKGROUND OF THE INVENTION

It has been demonstrated that part of the function of the immune system is elimination of tumors (Steer, et al. (2010) *Oncogene* 29:6301-13; de Visser & Coussens (2006) *Contrib. Microbiol.* 13:118-37; Lollini, et al. (2006) *BMC Bioinformatics* 7:352). Almost without exception, any tumor that manifests clinically has evaded immune surveillance by developing multiple immunosuppression mechanisms, such as expressing immunosuppressive mediators or calling in immunosuppressive cells with chemoattractants (Zou, et al. (2005) *Nat. Rev. Cancer* 5:263-74; Cubillos-Ruiz, et al (2009) *J. Clin. Invest.* 119:2231-44; Cubillos-Ruiz, et al. (2009) *Future Oncol.* 5:1189-92; Cubillos-Ruiz, et al. (2010) *Cell Cycle* 9:260-8; Scarlett, et al. (2009) *Cancer Re.* 69:7329-37; de Visser & Coussens (2006) supra; Conejo-Garcia, et al. (2004) *Cancer Res.* 64:2175-82; Conejo-Garcia, et al. (2003) *Cancer Biol. Ther.* 2:446-51; Conejo-Garcia, et al. (2005) *Blood* 105:679-81). Supporting ongoing anti-tumor immune responses offers great promise to complement treatments targeting the tumor cell cycle or cellular signaling pathways, and already represent the most effective intervention against otherwise incurable melanomas (Dudley, et al. (2001) *J. Immunother.* 24:363-73; Rosenberg & Dudley (2004) *Proc. Natl. Acad. Sci. USA* 101:14639-45; Zitvogel & Kroemer (2009) *J. Clin. Invest.* 119:2127-30). However, it has become increasingly clear that effective strategies to break tumor-mediated immunosuppression will be required to elicit comparable protective anti-tumor immunity against the most lethal cancers. This is because effective antitumor T cell responses mediated by CD4 and CD8 T-cells are not effectively activated in immune-suppressed tumor environments unless the immunosuppression can be reversed.

Immunotherapies are of particular interest for dealing with metastatic disease since the immune system is uniquely capable of identifying and eliminating small undetectable metastases. Ovarian carcinoma is a particularly promising target for novel immunotherapies in this context for a variety of reasons. First, ovarian cancer is typically diagnosed at an advanced stage as a metastatic disease with very poor prognosis. Second, multiple independent studies have confirmed that the magnitude of spontaneous but obviously suboptimal anti-tumor immune responses can predict the outcome of ovarian cancer patients (Hamanishi, et al. (2007) *Proc. Natl. Acad. Sci. USA* 104:3360-5; (Sato, et al. (2005) *Proc. Natl. Acad. Sci. USA* 102:18538-43; Zhang, et al. (2003) *Zhonghua Zong Liu Za Zhi* 25:264-7; Zhang, et al. (2003) *N. Engl. J. Med.* 348:203-213). Third, the 5-year survival rates of ovarian cancer patients have changed very little after 30 years targeting almost exclusively the tumor cell cycle, which urgently demands new complementary interventions. Fourth, even at a metastatic stage, ovarian cancer is most frequently found as a disease compartmentalized in the peritoneal cavity, which facilitates the adoptive transfer of immune cells or the application of adjuvants directly in the tumor microenvironment. Unfortunately, multiple immunosuppressive mechanisms converge at ovarian cancer locations to eventually abrogate both ongoing anti-tumor immunity and the effect of adoptively transferred tumor-reactive lymphocytes (Zou (2006) *Nat. Rev. Immunol.* 6:295-307; Nesbeth & Conejo-Garcia (2010) *Clin. Dev. Immunol.* 2010:139304; Kryczek, et al. (2007) *Am. J. Physiol. Cell Physiol.* 292:C987-95; Kryczek, et al. (2007) *J. Immunol.* 178:6730-3). Some of the most powerful immunosuppressive networks are orchestrated by regulatory T cells (Curiel, et al. (2004) *Nat. Med.* 10:942-9), as well as a variety of myeloid cells with overlapping phenotypic attributes of various lineages (Cubillos-Ruiz, et al. (2009) *J. Clin. Invest.* 119:2231-44; Scarlett, et al. (2009) supra; Curiel, et al. (2003) *Nat. Med.* 9:562-7; Huarte, et al. (2008) *Cancer Res.* 68:7684-91). In the microenvironment of solid ovarian tumor masses in both mice and humans, studies have identified massive recruitment of leukocytes with predominant phenotypic attributes of immature dendritic cells (DCs), including the expression of DEC205, CD11c, MHC-II, and CD8α. While these immature DC are immune-suppressed by the ovarian tumor, they possess the ability to phagocytose antigen in their tumor environment, and acquire the capacity to effectively present processed antigens in the right milieu (Cubillos-Ruiz, et al. (2009) supra; Scarlett, et al. (2009) supra). However, rather than boosting adaptive immune responses, ovarian cancer-associated DCs are not activated to mature, are strongly immunosuppressive, and support blood vessel formation, which promotes tumor development (Cubillos-Ruiz, et al. (2009) supra; Scarlett, et al. (2009) supra; Huarte, et al. (2008) supra). Adjuvant therapy that could mediate the maturation of these immature dendritic cells would reverse the immunosuppression and foster immunostimulation for therapeutic purposes. Such an approach could be used as a primary immunotherapy, as a conditioning therapy for adoptive T cell therapy, or as a therapy to boost T-cell antitumor responses.

The immune system has evolved to recognize and respond to microorganisms and therefore, microorganisms or their constituents are powerful adjuvants (Rakoff-Nahoum & Medzhitov (2009) *Nat. Rev. Cancer* 9:57-63). Each microorganism has unique characteristics in how they interact with the immune system and therefore each microorganism has unique adjuvant characteristics. Recently, the rapidly developing understanding about the interaction of innate and adaptive immunity and the associated understanding of how adjuvants work has fostered renewed interest in using microorganisms as adjuvants to stimulate antitumor immune responses (Paterson & Maciag (2005) *Curr. Opin. Mol. Ther.* 7:464-60; Paterson (2004) *Immunol. Res.* 27:451-62; Paterson & Ikonomidis (1996) *Curr. Opin. Immunol.* 8:664-9; Pan, et al. (1995) *Nat. Med.* 1:471-7; Pan, et al. (1995) *Cancer Res.* 55:4776-9; Pan, et al. (1999) *Cancer Res.* 59:5264-9; Sinnathamby, et al. (2009) *J. Immunother.* 32:856-69). This approach is strengthened by the ability to genetically manipulate the microorganisms to make them safer and more effective (Paterson & Ikonomidis (1996) supra). The focus of these studies has been on using *Listeria monocytogenes*, a gram positive bacterium that can live either within or outside of cells (Paterson & Maciag (2005) supra; Paterson (2004) supra; Paterson & Ikonomidis (1996) supra; Pan, et al. (1999) supra; Pan, et al. (1995) supra; Sinnathamby, et al. (2009) supra). Attenuated *Listeria* has been used in multiple phase I and II clinical trials against cervical, and prostate cancers (ClinicalTrial.gov Identifier NCT01116245, NCT00327652, NCT00585845, NCT0080007).

SUMMARY OF THE INVENTION

The present invention features a method for preventing or treating cancer by administering to a subject in need of treatment an effective amount of an attenuated mutant of *Toxoplasma gondii*. In some embodiments, the attenuated mutant includes a knockout mutation of one or more genes of the de novo pyrimidine synthesis pathway, e.g., a gene encoding carbamoyl phosphate synthetase II, aspartate transcarbamylase, dihydroorotase, dihydroorotase dehydrogenase, orotate phosphoribosyltransferase, or orotidine 5'-monophosphate decarboxylase. In another embodiment, the *T. gondii* is attenuated by γ-irradiation. In still other embodiments, the attenuated mutant expresses one or more tumor antigens or exogenous proteins. In yet other embodiments, the attenuated mutant is administered intravenously, intratumorally, or intraperitoneally and the cancer is ovarian cancer or melanoma.

BRIEF DESCRIPTION OF THE DRAWINGS

FIG. 1 shows that therapy with a CPS mutant of *T. gondii* cures established murine ovarian cancer. Using a two-dose protocol (8 and 20 days after tumor was implanted), mice were either not treated (untreated) or treated with the CPS mutant (treated). Tumor survival was monitored.

FIG. 2 shows that the survival advantage conferred by the CPS mutant is dependent on IL-12. ID8-Vegf Defb29 cells were implanted intraperitoneally into C57BL/6 (B6) or C57BL/6 mice that lack IL-12p35 (IL12p35 KO). Using a two-dose protocol (8 and 20 days after tumor was implanted), B6 and IL-12p35 KO mice were either not treated (untreated) or treated with the CPS mutant (treated). Tumor survival was monitored. Shown is the compilation of four independent experiments, wherein the survival advantage in the most aggressive ID8-Vegf Defb29 model is 16 to 17 days on average.

FIG. 3 shows that CPS mutant treatment provides significant additional survival benefit. ID8-Vegf Defb29 cells were implanted intraperitoneally then mice were either not treated (naïve), or were treated 8 days later (1 dose); 8 and 20 days later (2 dose); 8, 20 and 32 days later (3 dose); 8, 20, 32, 44 and 56 days later (5 dose); or 8, 20, 32, 44, 56, 68, and 70 days later (7 dose) with CPS and tumor survival was monitored.

FIG. 4 shows that therapy with CPS mutant cures established melanoma (FIG. 4B) compared to control phosphate-buffered saline (PBS)-treated mice (FIG. 4A). For this study, intratumoral injection started on day 9 when the tumor was 4 mm and was further carried out on days 9, 10, 13, and 14.

FIG. 5 shows the effect of γ-irradiation on anti-tumor activity of *T. gondii*. Aggressive ID8-Vegf Defb29 cells were implanted in mice and the mice were not treated (naive) or treated with a single dose of the CPS mutant, γ-irradiated CPS mutant, or γ-irradiated parental strain RH. Each treatment provided essentially identical survival advantage of approximately 10 days.

DETAILED DESCRIPTION OF THE INVENTION

*Toxoplasma gondii*, an obligate intracellular apicomplexan parasite of mammals, has been shown to inhibit angiogenesis (Hunter, et al. (2001) *J. Immunol.* 166:5878-81; Kim, et al. (2007) *J. Korean Med. Sci.* 22:S38-46); *T. gondii* antigens have been shown to decrease fibrosarcoma growth (Darani, et al. (2009) *Korean J. Parasitol.* 47:175-7), enhance dendritic cell-based cancer vaccines (Motamedi, et al. (2009) *Clin. Vaccine Immunol.* 16:1393-8); and formalin-fixed *T. gondii* has been shown to exhibit antitumor activity (Suzuki, et al. (1986) *J. Biol. Response Mod.* 5:288-293). Using an attenuated mutant strain of *T. gondii* (i.e., CPS) that cannot replicate in vivo, but can elicit a strong Th1 immune response characterized by high local levels of IL-12 and IFN-γ and high systemic levels of IL-12p70, it has now been found that *T. gondii* serves as an antitumor adjuvant in cancer. The antitumor effects of the CPS mutant in ovarian cancer start with the infection and subsequent maturation of immature immunosuppressive dendritic cell, wherein the maturation of these dendritic cells stimulates anti-tumor immunity against the cancer by changing the microenvironment from immunosuppressive to immunostimulatory.

Accordingly, the present invention provides a method for the prevention and treatment of cancer using vaccine containing an attenuated mutant of *T. gondii*. As is conventional in the art, the term "attenuated" refers to a weakened and/or less vigorous strain of *T. gondii*. Desirably, the attenuated mutant of the invention is capable of stimulating an immune response and creating immunity but not causing illness. Attenuation can be achieved by conventional methods including, but not limited to, γ-irradiation or the generation of a pyrimidine auxotroph. A pyrimidine auxotroph of the invention can be generated by disrupting mechanisms for pyrimidine acquisition including, mutating proteins involved in pyrimidine synthesis along with those of pyrimidine salvage (e.g., enzymes or transporters). Specifically, pyrimidine auxotrophs can be produced by knocking out or mutating one or more of CPSII (carbamoyl phosphate synthetase II; Gene loci ID 583.m05492), OMPDC (orotidine 5'-monophosphate decarboxylase; Gene loci ID 55.m04842), OPRT (orotate phosphoribosyltransferase; Gene loci ID 55.m04838), DHO (dihydroorotase; Gene loci ID 83.m00001), aspartate transcarbamylase (ATC), dihydroorotase dehydrogenase (DHOD), uridine phosphorylase (UP), uracil phosphoribosyltransferase, purine nucleoside phosphorylase (e.g., PNP), or a nucleobase/nucleoside transporter of pyrimidine bases or nucleosides (e.g., NT2 or NT3). Indeed, any single knockout or combination of knockouts is contemplated to achieve an attenuated strain. By way of illustration, the present embraces an attenuated strain or vaccine strain constructed by a single knockout in any of the six de novo pyrimidine biosynthetic genes (CPS, ATC, DHO, DHOD, OPRT or OMPDC), knockout of two or more genes of the de novo pyrimidine synthetic pathway, or knockout of a de novo pyrimidine synthesis gene in combination with a knockout in a pyrimidine salvage gene (e.g., coding for enzymes UP, PNP, or uracil phosphoribosyltransferase) and/or in combination with a knockout of a nucleobase/nucleoside transporter of pyrimidine bases or nucleosides. Such attenuated mutants can be generated by substitution, deletion or insertion as is conventional in the art. It is contemplated that because an attenuated pyrimidine auxotroph of *T. gondii* (e.g., a CPSII or OMPDC knockout) induces a Th-1 immune response, any attenuated mutant of *T. gondii* can be used as a vaccine without the complication of dead host cells and infectious dissemination of *T. gondii* in the host. Thus, particular embodiments of the present invention embrace a vaccine including an attenuated pyrimidine auxotroph of *T. gondii*.

In addition to attenuation, mutants of the invention can be multiply crippled strains of *T. gondii* that exhibit other desirable defects such as loss of ability to develop into tissue cysts, loss of sexual stages, loss of oocyst formation, or other developmental or phenotypic defects or changes that would enhance the efficacy or safety of vaccines based on mutants of the invention. For example, while certain proteins have been shown to contain T-cell epitopes (e.g., GRA4, GRA6, and ROP7) and may be important in immunity, other proteins signal to host cells (e.g., ROP16, ROP18) and may present tools to manipulate mammalian cells. See Mercier, et al. (1998) *Infect. Immun.* 66:4176-4182; Lecordier, et al. (1999) *Mol. Biol. Cell.* 10(4):1277-87; Igarashi, et al. (2008) *Gen. Mol. Res.* 7(2):305-313. Therefore, certain embodiments of this invention embrace mutating or deleting any secreted protein of the parasite, for example one or more of the GRA genes (i.e., GRA2, GRA3, GRA4, GRA5, GRA6, GRA7, GRA8, and GRA9) and/or ROP genes (i.e., ROP16 and ROP18) to modify or improve the ability of attenuated *Toxoplasma* to present antigens in vaccine formulations. Such an approach could improve vaccine efficacy and provide insight into how to manipulate host cells for new therapeutics. The GRAs occupy the vacuole space or vacuole membrane, which are key intersections that exogenous antigens (i.e. a vaccine formulation expressed by attenuated *T. gondii*) must pass through to get presented onto the MHCI or MHCII of the host cell.

As is conventional in the art, a gene or locus is the coding region and expression control sequences (e.g., promoter, enhancer, and the like) of a protein. In the context of the present invention, a mutation includes a substitution, deletion, or insertion at the desired locus which decreases or abolishes the activity of the protein encoded by said locus. For example, amino acid substitutions or insertions at the enzyme active site are expected to significantly decrease or abolish activity. Similarly, amino acid substitutions or insertions which destabilize (e.g., enhance degradation) the desired mRNA or protein can be used to decrease or abolish the activity a protein, e.g., CPSII. Moreover, promoter mutations which decrease or abolish expression of a protein can be used to decrease or abolish activity. In particular embodiments, a mutant of the present invention lacks all or a substantial portion (e.g., more than 50, 60, 70, 80 or 90%) of the nucleic acids encoding a protein of interest. As is conventional in the art, the nucleic acids encoding a protein of interest include the nucleic acids beginning at the initiation codon (i.e., ATG) and ending at the termination codon (e.g., TGA, TAA and TAG). In some embodiments, a mutant of the present invention lacks all, or a substantial portion, of the nucleic acids encoding CPSII or OMPDC. Thus, in one embodiment, the attenuated mutant *T. gondii* of the invention is an attenuated CPSII or OMPDC knock out mutant.

A mutant of the present invention can be generated using any suitable method conventionally employed for producing gene knockout mutants of *T. gondii*. For example, the mutant can be obtained by the single cross-over integration, e.g., as disclosed by Fox & Bzik ((2002) *Nature* 415(6874):926-9) or using a double-crossover gene replacement, e.g., as disclosed by Mercier, et al. ((1998) *Infect. Immun.* 66:4176-82). See also Wang, et al. (2002) *Mol. Biochem. Parasitol.* 123(1):1-10, or by using KU80 mutant strains for precise gene replacement as described in U.S. Pat. No. 7,803,389, incorporated herein by reference. In general, the generation of a mutant *T. gondii* includes isolating the nucleic acid molecule of interest from *T. gondii*; replacing, mutating, substituting or deleting all or a portion (e.g., one or more bp) of the gene to disrupt the promoter, regulatory sequence(s) and/or coding region of the protein; and integrating the disrupted molecule (e.g., via single- or double-crossover homologous recombination events) into the genome of *T. gondii*. Upon selection, i.e., marker protein expression or genomic DNA analysis, a knockout mutant is obtained. In particular embodiments, the selectable marker is selected for by positive and negative selection (e.g., HXGPRT), such that the selectable marker can be easily deleted from the targeted locus by homologous recombination and, upon negative selection, recovered for use again in a sequential process of positive and negative selection to create strains harboring multiple gene knockouts or replacements. Disruption of all or a portion of a gene of interest can be achieved by, e.g., replacing the coding sequence with a nucleic acid molecule encoding selectable marker, replacing the coding sequence with a nucleic acid molecule encoding an exogenous protein, substituting the promoter with a mutated promoter which can no longer be recognized by *T. gondii* transcription proteins (i.e., a promoter mutation), etc. As is known to the skilled artisan, subsequent restriction endonuclease digestion and Southern blot analysis of the mutant *T. gondii* genomic DNA can be used to confirm the knockout.

As will be appreciated by the skilled artisan, any suitable marker-encoding nucleic acid can be used to identify a *T. gondii* which has been transformed so long as it can be phenotypically detected in the mutant strain. Suitable marker proteins include, but are not limited to, positive and negative selectable markers such as HXGPRT, thymidine kinase, hygromycin resistance, cytosine deaminase, DHFR (dihydrofolate reductase), bleomycin, chloramphenicol acetyl transferase, or combinations thereof. It is contemplated that the nucleic acid molecule encoding the marker protein can be used to replace or substitute all or a portion of the promoter or coding sequence of the locus of interest to generate a knockout or mutant.

In an alternative embodiment, the attenuated mutant *T. gondii* of the invention is a γ-irradiated attenuated mutant strain of *T. gondii*. The use of γ irradiation to attenuate *T. gondii* is described in the art (Dubey, et al. (1998) *Int. J. Parasitol.* 28:369-75; Kook, et al. (1995) *Korean J. Parasitol.* 33:173-8). Specifically, $^{137}$Cs irradiation of sporulated oocysts has been shown to yield infective sporozoites, which are capable of penetrating enterocytes and all cells in the lamina propria, but not capable of inducing a viable infection. In particular, when attenuated by γ irradiation, it is desirable that the attenuated mutant maintain the ability to invade cells, including DC and myeloid cells, to provide optimal antitumor responses. In this respect, it has been demonstrated that a killed CPS mutant (non-invasive) does not provide the tumor survival benefit. Given that invasion injects specialized parasite effector molecules into the host cell cytoplasm thereby seizing control of the host cell (Butcher, et al. (2011) *PLoS Pathogens* 7(9):e1002236; Fentress, et al. (2010) *Cell Host Microbe* 8(6):484-95; Jensen, et al. (2011) *Cell Host Microbe* 9(6):472-83; Saeij, et al. (2006) *Science* 314(5806):1780-3; Taylor, et al. (2006) *Science* 314(5806):1776-80; Saeij, et al. (2007) *Nature* 445(7125):324-7; Peixoto, et al. (2010) *Cell Host Microbe* 8(2):208-18), invasion is a key component to the effectiveness of using *T. gondii* in a vaccine.

While mutants of the present invention can be produced from a virulent type I strain such as RH (as exemplified herein), a type II strain as well as a type III strain can also be employed so that the underlying development of tissue cysts as well as oocysts in *Toxoplasma* infection can be analyzed.

While the instant mutant *T. gondii* may be used as is in the prevention or treatment of cancer, the instant mutant can also be further modified to deliver one or more tumor antigens. Specific examples of tumor antigens include, but are not limited to, mesothelin, CEA, p53, Her2/neu, ErB2, melan A, MAGE antigens, nm23, BRACA1, and BRACA2. In one embodiment, the tumor antigen is expressed by *T. gondii*, secreted into the parasite vacuole and eventually into the cytosol of the mammalian host cell. The *T. gondii*-expressed tumor antigen subsequently enters the mammalian antigen presenting cell's (APC) antigen processing and presenting pathway as a substrate for generation of class I and class II peptides which generate CD8 and CD4 T cell responses. Accordingly, in one embodiment of the present invention, an attenuated mutant of the invention harbors nucleic acid molecules encoding one or more tumor antigens.

It is further contemplated that an attenuated mutant of *T. gondii* can be used to express any exogenous protein one would want to express within a mammalian host cell. This could include therapeutic peptides or proteins, e.g., therapeutic antibodies (e.g., Trastuzumab) proteins (e.g., interferons, blood factors, insulin, erythropoietin, and blood clotting factors), or enzymes (e.g., asparaginase, catalase, lipase, and tissue plasminogen activator) used in the treatment of diseases or conditions. Such proteins are routinely expressed in other systems, e.g., yeast, mammalian cells lines, bacteria or insect cells, such that one skilled in the art could readily obtain nucleic acids encoding such proteins and express them in a mutant *T. gondii*.

The *T. gondii* mutant of the present invention can accommodate multiple expression constructs. Therefore, nucleic acid molecules encoding exogenous proteins, antigens and the like can be integrated into the *T. gondii* genome, e.g., as part of the nucleic acid molecule used to disrupt the promoter, regulatory sequences, or open reading frame of a protein of the pyrimidine synthesis pathway or at any other suitable location in the genome (e.g., at non-essential locus).

The basic criteria for exogenous protein and tumor antigen expression are that the gene is a non-*T. gondii* gene or coding sequence and the gene or coding sequence is able to be expressed directly or indirectly from a recombinant molecule in a *T. gondii* cell. In this regard, it is desirable that the promoter employed is recognizable by *T. gondii*. Moreover, it is desirable that the promoter promotes transcription of the protein coding sequence when the *T. gondii* is inside mammalian cells. To this end, particular embodiments embrace the use of a *T. gondii* promoter. Known promoter and other regulatory elements (e.g., 5' UTR, 3' UTR, etc.) which can be operably linked to the coding sequence of an exogenous protein of interest so that the exogenous protein is expressed in *T. gondii* include, but are not limited to, sequences from the *T. gondii* SAG1 gene (Striepen, et al. (1998) *Mol. Biochem. Parasitol.* 92(2):325-38) or the *T. gondii* NTPase gene (Robibaro, et al. (2002) *Cellular Microbiol.* 4:139; Nakaar, et al. (1998) *Mol. Biochem. Parasitol.* 92(2):229-39). Alternatively, suitable regulatory sequences can be obtained by known trapping techniques. See, e.g., Roos, et al. (1997) *Methods* 13(2):112-22. Promoters of use in accordance with the present invention can also be stage-specific promoters, which selectively express the exogenous protein(s) or antigen(s) of interest at different points in the obligate intracellular *T. gondii* life cycle. Moreover, it is contemplated that an endogenous promoter can be used to drive expression of the exogenous protein or antigen by, e.g., site-specific integration at the 3' end of a known promoter in the *T. gondii* genome.

When employed as a vaccine for generating an immune response and providing prevention or treatment of cancer, particular embodiments provide that the mutant *T. gondii* is in admixture with a pharmaceutically acceptable carrier. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000. Furthermore, it has now been shown that ex vivo loading of dendritic cells, macrophages, and peritoneal cells with a CPS mutant, then immunizing an animal with these loaded cells leads to successful immunization. For example, dendritic cells loaded with a CPS mutant provides the strongest immune response in animals and produces long lasting CD8 T cell responses and long lasting immune memory. Accordingly, it is contemplated that a *T. gondii* mutant of the invention which is also a pyrimidine auxotroph can be administered via loading of dendritic cells, macrophages, and/or peritoneal cells. Moreover, the use of irradiated tumor cells infected in vitro with a CPS mutant have been shown to exhibit potent anti-tumor activity in an animal model of ovarian cancer (all mice rejected rechallenge with tumor cells 150 days later). Therefore, as an alternative, the attenuated mutant can be administered via loading of irradiated tumor cells.

Administration of a mutant *T. gondii* disclosed herein can be carried out by any suitable means, including intraperitoneal, subcutaneous, intravenous or intramuscular injection, intratumoral, orally, intra-spinal, intra-cranial, intra-organ (for example pancreas), or by topical application (typically carried in a pharmaceutical formulation) to an airway surface. Topical application to an airway surface can be carried out by intranasal administration (e.g., by use of dropper, swab, or inhaler which deposits a pharmaceutical formulation intranasally). Oral administration can be in the form of an ingestible liquid or solid formulation. In particular embodiments, a *T. gondii* mutant is formulated for administration via intraperitoneal, intranasal or intravenous routes.

An attenuated mutant *T. gondii* or vaccine containing the same can be employed in various methods inducing an immune response and preventing or treating cancer. Such methods generally involve administering to a subject in need of treatment an effective amount of an attenuated mutant *T. gondii* or vaccine of the present invention thereby generating an immune response and preventing or treating the subject's cancer. Cancers that can be prevented or treated with the instant attenuated mutant *T. gondii* or vaccine include, but are not limited to, primary or secondary cancers of the brain, skin, pancreas, liver, ovary, breast, prostate, lung, colon, cervix, bone, bladder, stomach, testis, thyroid, kidney, throat, mouth, uterus, rectum or esophagus. In particular embodiments, the cancer is ovarian cancer or melanoma.

An effective amount, as used in the context of the instant invention, is an amount which produces a detectable immune response (e.g., a Th-1 response, natural granulocyte, neutrophil, macrophage, GR1+ macrophage, B cell, or T cell immune response) or antibody production and reduces or prevents the signs or symptoms of cancer. In accordance with some embodiments, the *T. gondii* mutant expresses an exogenous antigen thereby generating protective immunity against the cancer from which the antigen was derived or associated. However, in other embodiments, the *T. gondii* mutant of the invention alone is sufficient to generate an immune response thereby treating or having effect on the severity of the cancer. For example, using an attenuated γ-irradiated mutant in a model of highly aggressive ovarian cancer or an attenuated uracil auxotroph mutant in two different cancer models of aggressive ovarian cancer and aggressive melanoma cancer it was shown that administration of the vaccine platform alone provided a cure or near cure in mice with already established late stage aggressive ovarian cancer or aggressive melanoma. Accordingly, an effective amount of a *T. gondii* mutant of the invention prevents or treats the signs or symptoms of cancer, or diminishes cancer progression or spread (e.g. metastasis). Responses to administration can be measured by analysis of subject's vital signs, monitoring T cell responses, monitoring production of IFN-γ, IL-12p40, and/or IL-12p70, or monitoring chemokines CCL5 or CXCL1 according to the methods disclosed herein or any suitable method known in the art.

While the instant compositions and methods find application in the prevention and treatment of cancer in mammals, in particular humans, the invention should be construed to include administration to a variety of animals, including, but not limited to, cats, dogs, horses, cows, cattle, sheep, goats, birds such as chickens, ducks, and geese. Subjects benefiting from prophylactic or therapeutic treatment with the instant attenuated mutant *T. gondii* include subjects with a positive diagnosis of early or late stage cancer, subjects at risk of developing cancer (e.g., because of family history or exposure to a carcinogen), and subjects who have had successful treatment of a primary tumor and are at risk of developing or have developed a secondary or metastatic tumor.

The precise schedule for administration can be determined by a skilled practitioner. Administration can be given initially in a single dose schedule, or by rapid priming of multiple repeated doses spaced 6 to 24 hours apart. This initial treatment can be followed by a multiple dose schedule in which a primary course of treatment can be with 1-10 separate doses, followed by other doses given at subsequent time intervals required to maintain and or reinforce the response, for example, at 12 days to 4 months for a second dose, and if needed, subsequent dose(s) after several weeks or months.

The exact dosage for administration can be determined by the skilled practitioner, in light of factors related to the subject that requires prevention or treatment. Dosage and administration are adjusted to provide sufficient levels of the composition or to maintain the desired effect of preventing or reducing signs or symptoms of cancer, or reducing severity of the disease. Factors which may be taken into account include the severity of the disease state, general health of the subject, age, weight, and gender of the subject, diet, time and frequency of administration, drug combination(s), reaction sensitivities, and tolerance/response to therapy.

The following non-limiting examples are provided to further illustrate the present invention.

EXAMPLE 1

Materials and Methods

Mice. Wild-type C57BL/6 were purchased from the National Cancer Institute or Jackson Labs, and IL-12p35$^{-/-}$, IL-12p40$^{-/-}$, and Myd88$^{-/-}$ mice were purchased from The Jackson Laboratory. Animal experiments were approved by the Institutional Animal Care and Use Committee at Dartmouth Medical School.

Cell Lines and Parasites. ID8-Defb29/Vegf-A or ID8-Vegf-A flank tumors or intraperitoneal tumors were generated according to known methods (Conejo-Garcia, et al. (2004) supra). Tumor volumes were calculated as $0.5\times(l\times w^2)$, where l is length and w is width.

Toxoplasma gondii RH strain or attenuated uracil auxotroph mutants cps1 (CPS) and yellow fluorescent protein (YFP) YFP-cps1 (YFP-CPS) were cultured according to known methods (Fox & Bzik (2002) Nature 415(6874): 926-9). In some experiments, tachyzoites were further inactivated by γ-irradiation (15 krad).

Survival Experiments. Mice were intraperitoneally injected with $2\times10^6$ ID8-Defb29/Vegf-A ovarian or $2\times10^6$ ID8-Vegf A ovarian carcinoma cells, and mice were treated at days 8 and 20 (unless otherwise stated) after tumor challenge with $2\times10^6$ or $1\times10^7$ CPS. To generate an anti-Toxoplasma immune response, mice were immunized twice, 14 days apart, with $2\times10^6$ CPS. The immune mice were then challenged with the virulent RH strain of T. gondii ($5\times10^6$) and all immune mice survived. Nine months later, the immune mice were challenged with ID8-Defb29/Vegf-A ovarian carcinoma cells then treated or not treated with $2\times10^6$ CPS parasites.

Flow Cytometry and Cytokine Assay. Flow cytometry was performed on a FACS-CANTO system (BD Biosciences). Cell populations were sorted from peritoneal washes (10 ml PBS) of ovarian carcinoma-bearing mice using a FACS ARIA sorter (BD Biosciences).

ELISPOT. Total cells were obtained from peritoneal washes of treated or untreated ID8-Defb29/Vegf-A tumor-bearing mice. Peritoneal cells were co-cultured with bone marrow-derived dendritic cells (DC) at a 10:1 ratio for 48 hours in coated and blocked ELISPOT plates. The DC were previously pulsed (overnight) with doubly irradiated (Gamma and UV-treated) ID8-Defb29/Vegf-A cells (10 dendritic cells:1 tumor cell). All cultures were maintained in complete RPMI containing 10% fetal bovine serum. Analysis was carried out according to the manufacturer's protocol (eBioscience).

Cytokine Detection Via ELISA. Peritoneal lavages (10 mL PBS) were used in ELISA assays for interleukin 12 (p70) (Biolegend), interleukin 23 (Biolegend), and CCL2 (eBioscience) according to the manufacturers' instructions.

Mouse-23-Plex LUMINEX. A panel cytokine assay (BIO-RAD) was used to detect (IL1a, IL1b, IL2, IL3, IL4, IL5, IL6, L8, IL9, IL10, IL12p40, IL13, IL17, eotaxin, G-CSF, GM-CSF, INF-g, MCP-1a, MIP-1b, CCL5, KC-1 TNF-a) following the manufacturer's instructions.

In Vivo Antigen Processing. Mice bearing ID8-Defb29/Vegf-A tumors for three weeks were intraperitoneally injected with 250 μg fluorogenic DQ-OVA (Invitrogen); four hours later, mice received a single intraperitoneal injection of $1\times10^7$ YFP expressing CPS, 18 hours later peritoneal cells were harvested and processing of the fluotogenic probe by DCs was determined by FACS.

In Vivo OT-1 CFSE Dilution Assay. ID8-Defb29/Vegf-A tumor bearing mice were i.p. injected (21 days post-tumor challenge) with 0.6 mg of full-length endotoxin-free OVA (SIGMA, grade VII). Four hours later, mice received $1\times10^7$ CPS i.p. and 18 hours after that mice were injected i.p. with $2\times10^6$ CFSE-labeled OT-1 CD3$^+$ cells (negatively, purified using MACS, Miltenyi Biotec) that were harvested from spleens and lymph nodes of OT-1 mice. Forty-eight hours post-transfer of the T cells, FACs was performed on peritoneal wash from treated and non-treated CPS mice to measure cell division (CFSE dilution).

CFSE-Labeling. T cells were stained in a small volume of RPMI media with 10 μM of CFSE for 10 minutes at 37° C. in the dark. The staining was halted by addition of excess volume of RPMI and 2× wash with RPMI.

Anti-Mouse Antibodies. Antibodies were specific for CD45 (eBioscience), CD69 (eBioscience), CD11c (BD Biosciences), DEC205 (Serotec), MHC-II (eBioscience), CD3 (eBioscience), CD8b (eBioscience), CD44 (SouthernBiotech), CD62L (eBioscience), CD80 (eBioscience), CD86 (eBioscience), CD11b (eBioscience), B220 (eBioscience), NK1.1 (Biolegend) F4/80 (eBioscience), Tetramer Class I iTag MHC Tetramer (Beckmen Coulter).

Spleen Cell Type Characterization. A FACSCANTO flow cytometer was used to characterize spleen and peritoneal cellular make-up of treated and untreated ID8-Defb29/Vegf-A tumor bearing mice. Cell types were defined by surface markers: CD8 T cells (CD45$^+$, CD3$^+$, CD8$^+$), CD4 T cells (CD45$^+$, CD3$^+$, CD8$^-$), dendritic cells (CD45$^+$, CD11c$^+$), Natural killer cells (CD45$^+$, NK1.1$^+$, MHCII$^-$), macrophage (CD45$^+$, F4/80$^+$, CD11b$^+$,), and B cells (CD45$^+$, B220$^+$).

Statistical Analyses. Differences between the means of experimental groups were analyzed using the Mann-Whitney test. Mouse survival data were analyzed with the log-rank test. Data analysis was performed using Prism software (version 4.0; GRAPHPAD). A P value less than 0.05 was considered significant.

EXAMPLE 2

CPS Stimulates T Cell Expansion in Tumor-Bearing Hosts

The ability of the CPS mutant to enter viable cells and induce a powerful Th1 immune response in healthy hosts when injected intraperitoneally, indicated its potential as an adjuvant to break antitumor immunity against orthotopic ovarian cancer. Because the CPS mutant is not able to replicate in vivo and lacks any sort of toxin expression, it does not kill cells that it infects (Fox, et al. (2004) supra).

To fully test for any toxicity of the CPS mutant in vivo, severely immunodefficient NOD/SCID IL-2γ receptor knockout mice were challenged with $5\times10^6$ tachyzoites of the CPS mutant injected intraperitoneally. As with untreated mice, mice administered the CPS mutant showed no signs of toxicity and survived for >4 weeks. In addition, the CPS mutant did not induce any significant increase in the activity of hepatic enzymes or creatinine, demonstrating that, even in the most severely immunocompromised hosts available, the CPS mutant did not mediate obvious toxicity.

To determine how the CPS mutant impacts the immunological environment in ovarian cancer-bearing hosts, $2 \times 10^6$ tachyzoites of the CPS mutant were intraperitoneally administered to mice previously growing orthotopic, aggressive ID8-Defb29/Vegf-a tumors (Conejo-Garcia, et al. (2004) supra; Cubillos-Ruiz, et al. (2009) supra; Nesbeth, et al. (2010) supra; Nesbeth, et al. (2009) supra; Scarlett, et al. (2009) supra) for eight days. Interestingly, splenomegaly occurred in all treated mice, and the total number of CD4 and CD8 T splenic cells dramatically increased. Correspondingly, a significant expansion of total immune cells was observed at tumor (peritoneal) locations, where the proportions and absolute numbers of cytotoxic T cells (CTLs) were increased by over 4-fold, but the proportion of CD4 T lymphocytes were not increased. Furthermore, intraperitoneal administration of the CPS mutant to advanced ovarian cancer-bearing mice induced, at tumor locations, the up-regulation of multiple cytokines involved in classical Th1 responses, including the inducible p40 subunit of IL-12, biologically active IL-12p70, IFN-γ and CCL5, the latter of which is associated with a better prognosis in human and mouse ovarian cancer (Nesbeth, et al. (2010) supra; Zhang, et al. (2003) supra).

The strong peritoneal CCL5 chemokine response to CPS promotes cellular responses that are potentially beneficial in ovarian cancer. Angiogenesis promotes ovarian tumor progression as well as B16.F10 melanoma tumor progression. Treatment with CPS mutant markedly decreased peritoneal expression of the pro-angiogenic chemokine CXCL1. While this study did not assess CD4+ T-regulatory cells, this cell population promotes progression of ovarian cancer and B16.F10 melanoma. *Toxoplasma* infection was recently shown to reduce the CD4+ T-regulatory cell populations at the site of infection (Oldenhove, et al. (2009) *Immunity* 31:772-86). Thus, while multiple mechanisms are likely to contribute to downstream antitumor responses to the CPS mutant, this study indicates the early role of the CPS mutant in rapidly reversing tumor-induced immune suppression and in activating tumor antigen-specific CD8 T cell responses.

EXAMPLE 3

Effect of the CPS Mutant on Dendritic Cells

It has been shown that large numbers of myeloid cells, with predominant phenotypic attributes of immature DCs, infiltrate solid ovarian cancers in mice and humans, where they exert an immunosuppressive/pro-angiogenic activity (Cubillos-Ruiz, et al. (2009) supra; Cubillos-Ruiz, et al. (2009) supra; Conejo-Garcia, et al. (2005) supra; Conejo-Garcia, et al. (2004) supra). It was therefore posited that tumor-associated DCs were responsible for the observed dramatic up-regulation of immunostimulatory IL-12.

To identify the tumor microenvironmental cell types preferentially targeted by intraperitoneally administered CPS mutant, late-stage ID8-Vegf Defb29 tumors were established for 30 days, mice were treated by peritoneal injection of YFP-CPS (a CPS mutant strain engineered to express yellow fluorescent protein) and samples were analyzed 18 hours later. YFP-CPS primarily targeted CD45+ cell types for invasion in the peritoneum (~90%), whereas only 10% of CPS mutant-invaded cells were of nonhematopoietic origin. It was observed that 93.3% of CPS mutant-invaded CD45+ cells were CD11c+, indicating that the CPS mutant selectively invaded ID8-Vegf Defb29 tumor-associated CD11c+ DCs.

Immature immunosuppressive tumor CD11c+ DCs have been shown to phagocytose tumor antigen in the ovarian tumor environment (Scarlett, et al. (2009) supra). In untreated mice these immunosuppressive tumor DCs failed to display expression of co-stimulatory molecules CD80 or CD86, failed to process phagocytosed antigen, and consequently, the untreated tumor environment failed to cross-present antigen to CD8+ T cells. By contrast, in mice treated with YFP-CPS, parasite-invaded CD11c+ DCs significantly upregulated expression of co-stimulatory molecules CD80 and CD86, and they processed phagocytosed antigen. Furthermore, YFP-CPS-treated mice efficiently cross-presented antigen to CD8 T cells. A maturation effect was also apparent in bystander DCs that were not invaded by the CPS mutant. Bystander CD11c+ DCs showed an increase in CD80 expression, although no significant increase in expression of CD86 was observed. This bystander effect could reflect microbial sensing by tumor DCs, or alternatively, could be explained by recent observations that *Toxoplasma* often injects parasite effector molecules into bystander cells that are contacted by the parasite extracellularly but are not invaded. These results revealed that YFP-CPS rapidly converted the immunosuppressive ovarian tumor environment into an immune-activated environment. Parasite invasion of immature tumor-resident CD11c+ DCs activated this cell type to mature and restored the ability to prime CD8 T cell responses.

Because tumor-associated DCs spontaneously phagocytize tumor materials (Scarlett, et al. (2009) supra), it was subsequently determined how the CPS mutant impacts antigen processing by tumor DCs. For this analysis, a fluorogenic, full-length ovalbumin (OVA) compound (DQ-ova), which generates fluorescence upon proteolytic cleavage (Scarlett, et al. (2009) supra), was used. Notably, the fluorescent signal of intracellularly processed DQ-ova was significantly stronger in tumor-associated DCs from CPS mutant-treated mice, compared to untreated controls. While a detectable increase in antigen processing was observed in uninfected bystanders DCs from the CPS-treated tumor microenvironment, OVA antigen processing was markedly upregulated specifically in DCs that were directly invaded by the CPS mutant.

To determine whether increased antigen processing results in enhanced presentation of antigen to T cells and associated T cell activation, specifically at tumor locations, full-length OVA was intraperitoneally administered to advanced ovarian cancer-bearing mice. After 4 hours, mice were treated with the CPS mutant ($2 \times 10^7$ tachyzoites), and CFSE-labeled OT-1 transgenic T cells were subsequently transferred intraperitoneally 18 hours after CPS mutant exposure. Supporting previous observations about the antigen-presenting capacity of tumor DCs, very little OT-1 T cell proliferation was observed in the absence of CPS mutant treatment. In contrast, T cell proliferation, in response to OVA processed and presented at ovarian cancer locations, was dramatically enhanced in CPS mutant-treated mice. Therefore, the CPS mutant preferentially invades DCs at ovarian cancer locations, and transforms these DC, and to some degree bystander DC, from a tolerogenic to a strongly immunostimulatory cell type that effectively processes and presents phagocytized local antigens to prime T cell responses in situ.

EXAMPLE 4

The CPS Mutant Boosts T Cell-Mediated Antitumor Immunity

It was subsequently determined how increased maturation, antigen presentation and inflammatory cytokine secretion by DCs affected spontaneous T cell-mediated antitumor immunity. It was observed that ovarian cancer-bearing mice inoculated with the CPS mutant had significantly increased numbers (and proportions) of total activated (CD69$^+$) and antigen-experienced (CD44$^{hi}$) CD8$^+$ T cells at tumor locations. Most importantly, the number of T cells producing cytotoxic Granzyme B in response to tumor-antigen in ELISPOT analysis was also significantly increased, which, along with the elevated IFN-γ levels, further reflected T cell activation. Correspondingly, the absolute number and proportion of CD8$^+$ T cells recognizing a tetramer presenting the optimized ID8 tumor-antigen peptide Ala-Thr-Val-Thr-Asn-Val-Ser-Gly-Leu (SEQ ID NO:1) from the serologically defined breast cancer antigen (GENBANK Accession No. NM_025516) was accordingly increased. Moreover, tetramer-positive cells were antigen experienced (CD44$^{hi}$) and showed markers of recent activation (CD69$^+$).

At lymphatic (splenic) locations, much higher numbers and proportions of CD8$^+$ T cells showing phenotypic attributes of central memory differentiation, including the co-expression of CD44 and CD62L, were observed. As in the peritoneal cavity, the spleen contained significantly increased proportions and numbers of tumor-reactive (tetramer-specific) lymphocytes.

EXAMPLE 5

Adoptive Transfer of T Cells from CPS Mutant-Treated, Tumor Bearing Mice Transfers Tumor Immunity To define how anti-tumor T cells elicited by the CPS mutant exert biologically relevant immune pressure against ovarian cancer, T-cell transfer experiments were performed. Identical numbers of negatively immunopurified T cell splenocytes from CPS mutant treated or untreated ovarian cancer-bearing mice, as well as T cells from naïve mice, were transferred into different groups of healthy mice.

Untreated mice developed large tumors (approximately 1800 mm$^3$) and adoptive transfer of T cells from tumor-bearing (untreated) mice transferred a measurable antitumor activity based on a reduction in tumor volume (approximately 600 mm$^3$). This result is consistent with evidence showing that the ID8-Vegf Defb29 ovarian tumor is immunogenic and spontaneously generates measurable, although suboptimal antitumor T cell responses (Nesbeth & Conejo-Garcia (2010) supra). In contrast, adoptive transfer of T cells from tumor-bearing mice that were previously treated with the CPS mutant significantly reduced the tumor volume (approximately 90 mm$^3$), demonstrating that the CPS mutant elicited T cell populations in tumor bearing mice that effectively suppressed ovarian tumor development.

EXAMPLE 6

Novel CPS Mutant-Based Therapy Cures Aggressive Murine Ovarian Cancer

Figure 1A:
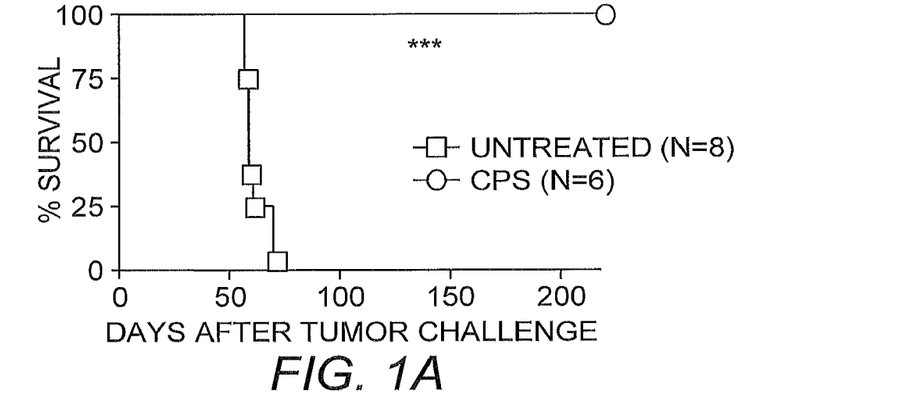
FIG. 1A, i.p. injected CPS mutant ($1 \times 10^7$) cured ovarian cancer (ID8/Veg-f) compared to untreated control.
Figure 1B:
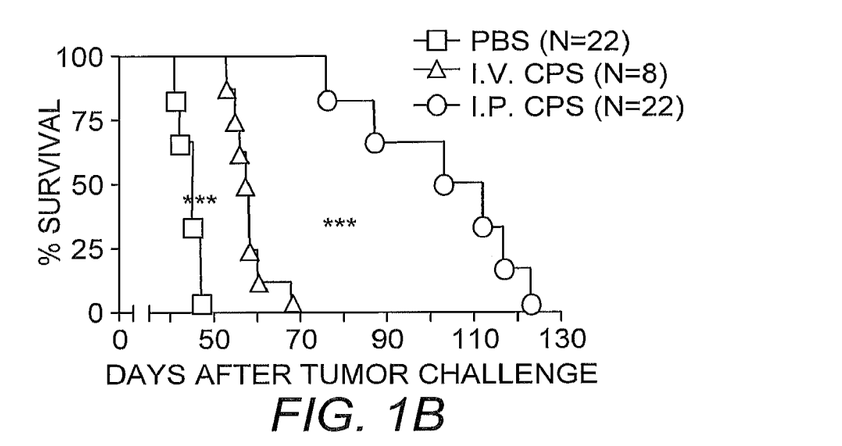
FIG. 1B, CPS mutant ($2 \times 10^6$) injected i.p. (local) or i.v. (systemically) yielded a significant survival advantage after ID8-Defb29/vegf-A challenge.
Figure 2:
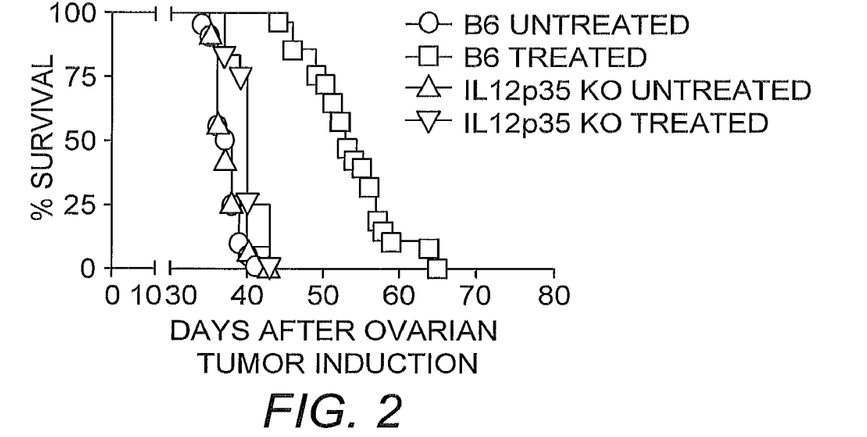

To determine the therapeutic potential of the anti-tumor immune response elicited by the CPS mutant against established orthotopic ovarian cancer, the CPS mutant was administered to mice at multiple doses and times. Mice were treated eight days and again at 20 days after highly aggressive ID8-Vegf Defb29 tumors had been established. Mice treated with the CPS mutant exhibited a significant survival advantage (FIG. 1A). Furthermore, this survival advantage was dependent on parasite invasion as well as IL-12 production (FIG. 2), but surprisingly was independent of the TLR adaptor molecule MyD88. Cps1 mutant treatment in the aggressive ID8-Vegf ovarian tumor model (Conejo-Garcia, et al. (2004) supra) was also examined. Treatment with the CPS mutant effectively cured mice bearing ID8-Vegf ovarian tumors (FIG. 1B).

Figure 1C:
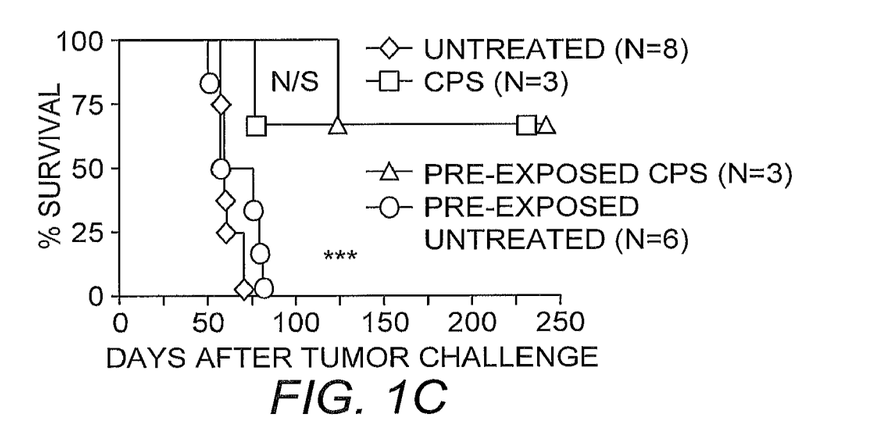
FIG. 1C, pre-exposure to the CPS mutant did not affect treatment efficacy of the CPS mutant ($2 \times 10^6$) in mice injected with tumor model ID8 (ID8/Veg-f).

*Toxoplasma* latently infects a substantial fraction of the world population and infected individuals possess life-long T-cell-based immunity. To examine whether preexisting immunity to *Toxoplasma* abrogates the effectiveness of CPS mutant treatment, mice were immunized using the CPS mutant to establish a life-long CD8 T-cell-based immunity. Immune mice were later challenged with intraperitoneal ID8-Vegf cells and were treated 8 days and 20 days later with the CPS mutant. Mice already immune to *Toxoplasma* exhibited similar increases in survival after CPS mutant treatment (FIG. 1C). Since immunity to *Toxoplasma* relies on IL-12 and IFN-γ responses and ultimately on memory CD8 T cell populations, the recall response to *Toxoplasma* challenge in the CPS mutant-immunized mice is rapid and effective. Preexisting immunity to *Toxoplasma* did not abrogate the effectiveness of the CPS mutant in stimulating antitumor responses to ovarian carcinoma.

Figure 3:
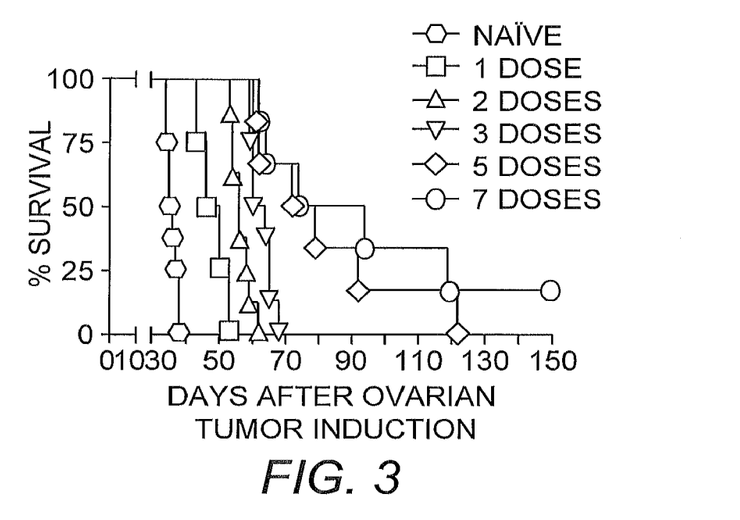

The effect of dosing was subsequently analyzed. As shown in FIG. 3, aggressive ID8-Vegf Defb29 cells were implanted and mice were subsequently treated with a 1, 2, 3, 5, or 7 doses of CPS mutant at 12 day intervals, but always giving the first dose 8 days after tumor implantation. These data show that each CPS mutant treatment provides significant additional survival benefit. Furthermore, since the mice in this experiment were immune by approximately day 25, the data further indicate that preexisting immunity does not abrogate treatment with the CPS mutant.

EXAMPLE 7

CPS Mutant Cures Melanoma Cancer

Figure 4A:
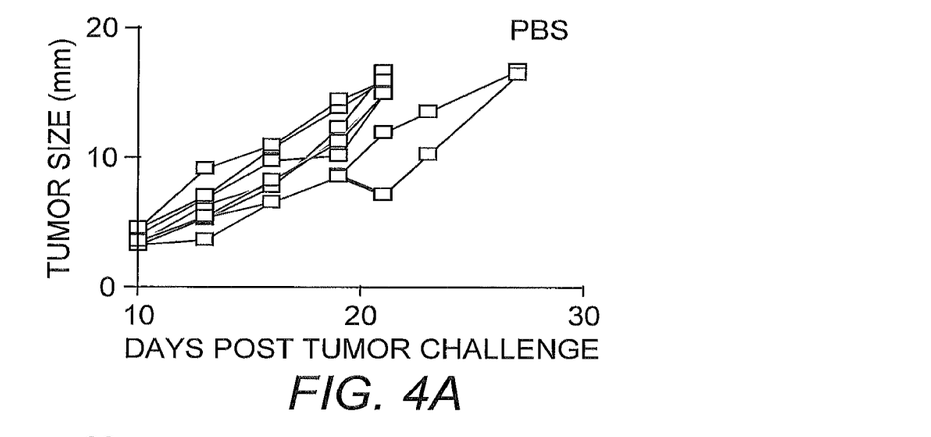
Figure 4B:
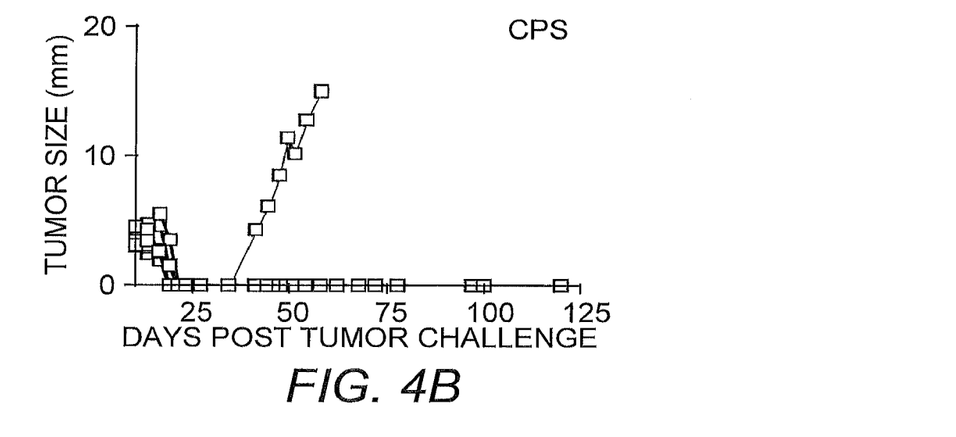

In contrast to the immunogenic ovarian tumor, the B16.F10 melanoma is weakly immunogenic. Accordingly, use of the CPS mutant in the treatment of melanoma was examined. The treatment for melanoma was direct injection of the CPS mutant (1.5×10$^7$) at day 11, 12, 15 and 16 after injection of B16 melanoma cells into mice. At the time of treatment, the average tumor size was in the range of 3.5-4 mm. Tumor size and survival were monitored. Intra-tumoral CPS mutant treatment of established B16.F10 melanoma halted tumor progression and the melanoma fully regressed to undetectable size (FIG. 4B) as compared to controls (FIG. 4A). The B16.F10 melanoma subsequently emerged at the original tumor site in most treated mice and increased in volume. Survival was significantly extended in the CPS mutant-treated mice, and surprisingly, a fraction of the CPS mutant-treated mice (~25%) remained B16.F10 melanoma-free. Indeed, subsequent analysis has indicated that 90% or more of mice can be cured of the primary tumor. Additionally, surviving tumor-free mice revealed a localized vitiligo indicating that the CPS mutant provoked a T cell based autoimmune response at the local tumor site. Autoimmune destruction of melanocytes, reflected phenotypically by vitiligo, was recently shown to provide self-antigen that increases protective memory CD8 T cell responses to B16.F10 melanoma.

EXAMPLE 8

Inactivation by γ-Irradiation does not Abrogate Antitumor Effects of CPS

Figure 5:
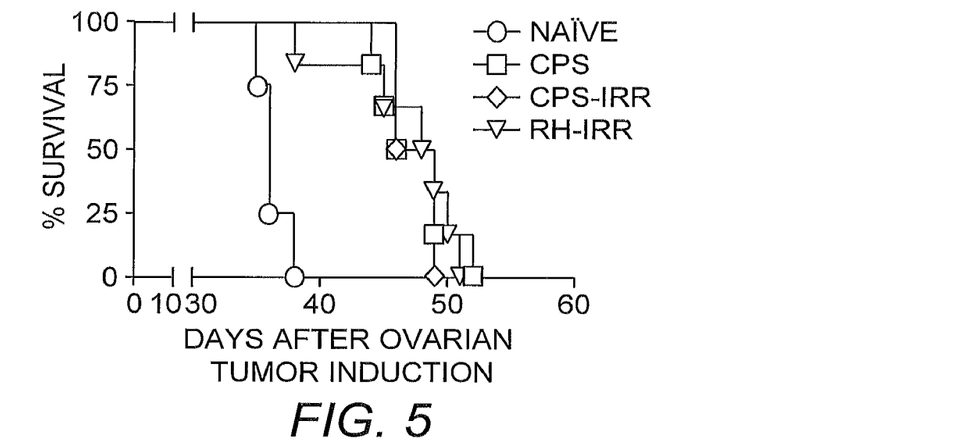

The CPS mutant or its parent strain RH were further inactivated by γ-irradiation. Eight days after tumor establishment, mice bearing highly aggressive ID8-Defb29/Vegf-a tumors were treated intraperitoneally once with CPS, with γ-irradiated CPS, with γ-irradiated RH, or left untreated. All treated mice showed similar and significant antitumor responses measured by increased survival time (FIG. 5). This data showed that γ-irradiation did not compromise the ability of CPS as an antitumor therapy and provides another strategy to inactivate and further attenuate mutant strains prior to cancer treatment.

What is claimed is:

1. A method for preventing or treating ovarian cancer comprising administering to a subject in need of treatment an effective amount of an attenuated mutant of *Toxoplasma gondii* that stimulates maturation of immature immunosuppressive dendritic cells and anti-tumor immunity to prevent or treat the subject's ovarian cancer.

2. A method for preventing or treating melanoma comprising administering to a subject in need of treatment an effective amount of an attenuated mutant of *Toxoplasma gondii* that comprises in its genome recombinant nucleic acid molecules encoding one or more melanoma antigens thereby preventing or treating the subject's melanoma.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Ala Thr Val Thr Asn Val Ser Gly Leu
1               5